United States Patent [19]

Kamstra

[11] Patent Number: 4,822,340
[45] Date of Patent: Apr. 18, 1989

[54] AUTOMATIC INJECTOR

[75] Inventor: Paulus R. Kamstra, Olst, Netherlands

[73] Assignee: Duphar International Research B.V., Weesp, Netherlands

[21] Appl. No.: 917,143

[22] Filed: Oct. 9, 1986

[30] Foreign Application Priority Data

Oct. 11, 1985 [NL] Netherlands ............... 8502777

[51] Int. Cl.⁴ .............................................. A61M 5/20
[52] U.S. Cl. ...................................... 604/135; 604/89;
  604/90; 604/191; 604/194; 604/199; 604/157
[58] Field of Search ........................... 604/89–91,
  604/135–136, 191, 194, 195, 196, 199, 231, 236,
  246, 247, 137, 134, 144, 157, 240, 243

[56] References Cited

U.S. PATENT DOCUMENTS

| | | | |
|---|---|---|---|
| 2,591,046 | 4/1952 | Brown . | |
| 2,717,601 | 9/1955 | Brown . | |
| 2,752,918 | 7/1956 | Uytenbogaart . | |
| 2,847,995 | 8/1958 | Adams . | |
| 2,866,458 | 12/1958 | Hein, Jr. . | |
| 2,888,924 | 6/1959 | Dunmire . | |
| 3,136,313 | 6/1964 | Enstrom et al. . | |
| 3,330,282 | 7/1967 | Visser et al. . | |
| 3,403,679 | 10/1986 | Sinclair et al. . | |
| 3,702,609 | 11/1972 | Steiner . | |
| 3,712,301 | 1/1973 | Sarnoff . | |
| 3,797,484 | 3/1974 | Sarnoff . | |
| 3,804,225 | 5/1974 | Allet-Coche | 604/90 |
| 3,881,484 | 5/1975 | Gidcumb, Jr. . | |
| 3,882,863 | 5/1975 | Sarnoff et al. . | |
| 3,914,419 | 10/1975 | Haeger et al. . | |
| 4,031,893 | 6/1977 | Kaplan et al. . | |
| 4,060,082 | 11/1977 | Lindberg et al. | 604/89 |
| 4,235,235 | 11/1980 | Bekkering . | |
| 4,394,863 | 7/1983 | Bartner . | |
| 4,496,344 | 1/1985 | Kamstra | 604/191 |
| 4,518,386 | 5/1985 | Tartaglia | 604/191 |
| 4,529,403 | 7/1985 | Kamstra | 604/136 |
| 4,573,472 | 3/1986 | Kamstra | 604/191 |
| 4,573,971 | 3/1986 | Kamstra | 604/191 |
| 4,599,082 | 7/1986 | Grimaud | 604/90 |

FOREIGN PATENT DOCUMENTS

| | | |
|---|---|---|
| 0072058 | 2/1983 | European Pat. Off. . |
| 1514210 | 2/1968 | France . |
| 7037845 | 6/1972 | France . |
| 871854 | 7/1961 | United Kingdom . |
| 1318803 | 5/1973 | United Kingdom . |

*Primary Examiner*—C. Fred Rosenbaum
*Assistant Examiner*—Mark F. Colosimo
*Attorney, Agent, or Firm*—Finnegan, Henderson, Farabow, Garrett & Dunner

[57] ABSTRACT

An automatic injector for injecting one or more different injection liquids, comprising a combination of a substantially cylindrical means containing a discharge mechanism and a plurality of cartridge elements. The cartridge elements comprise a piston in the substantially cylindrical means, a sealing stopper, a number of separating stoppers equal to one less than the number of the liquids, and a needle holder with injection needle. The needle holder comprises a stopper that is movable in the substantially cylindrical means and comprises a longitudinal bore. The injector comprises a by-pass means for injection liquid in front of the sealing stopper. In another embodiment the injection comprises a combination of a discharge mechanism, a cartridge holder and a cartridge, the cartridge comprising a barrel including the plurality of cartridge elements, wherein the by-pass for injection liquid comprises at least one duct recessed in the wall of the shaft of the needle holder, the needle holder being connected to the barrel, at least one aperture being recessed in the front of the shaft of the needle holder. In yet another embodiment, the injector is suitable for accommodating a solid and solvent therefor, and for that purpose comprises a solvent by-pass means and a passable stopper between the solid and the solvent, in which the solvent can pass the passable stopper by a telescoping movement of external components of the injector and can reach the solid, as a result of which the injector is made ready for use.

31 Claims, 6 Drawing Sheets

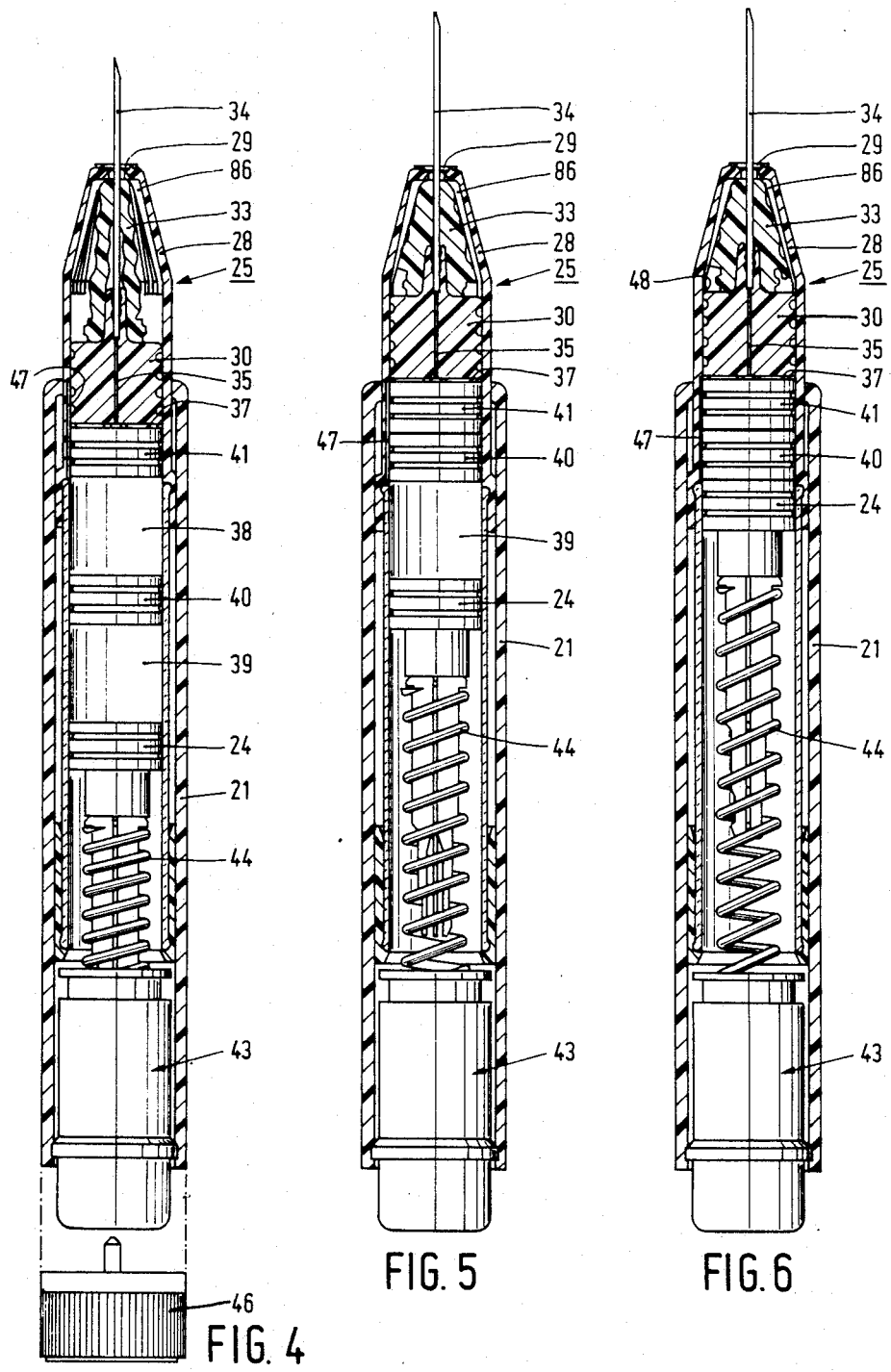

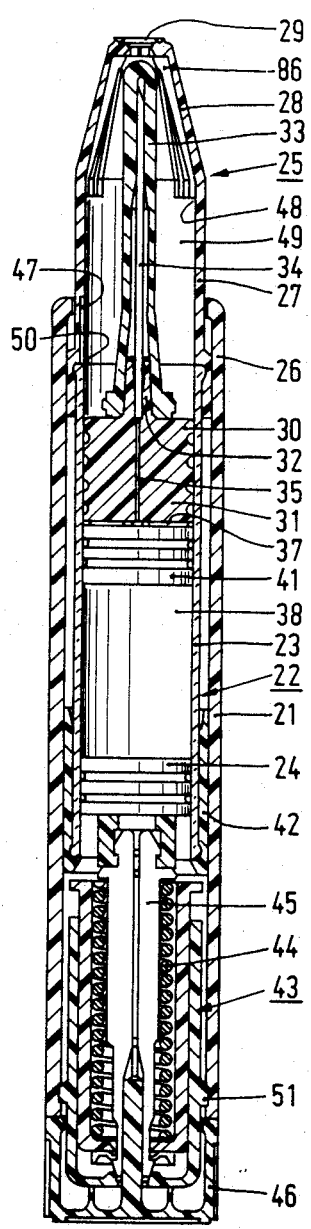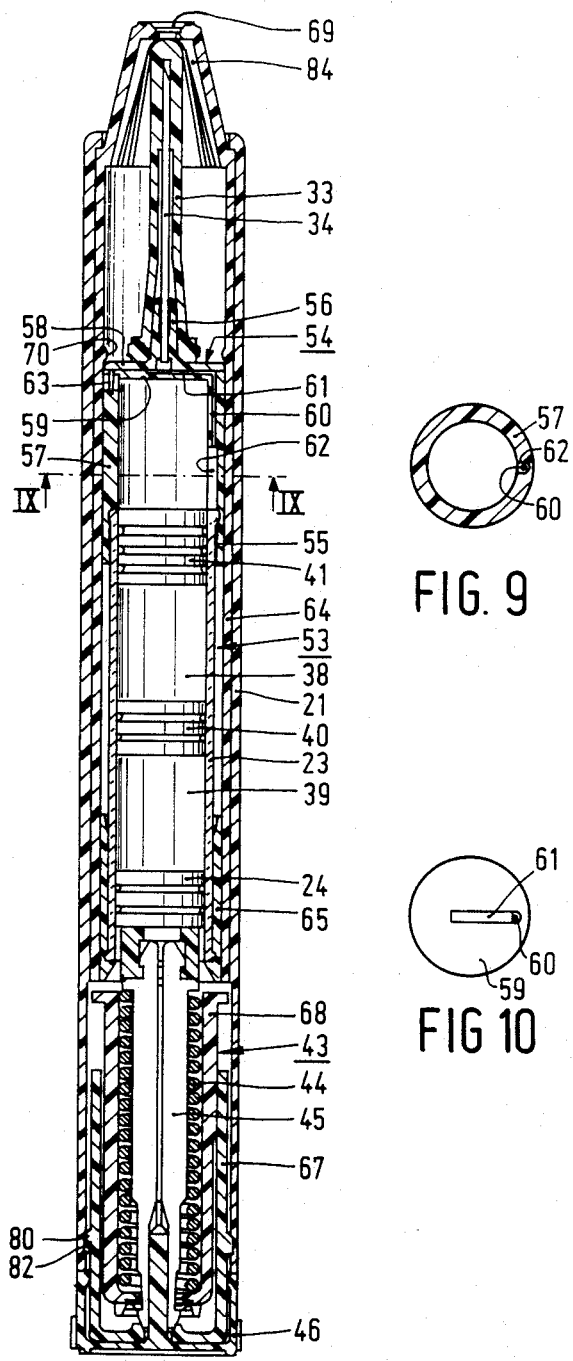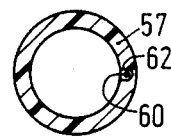
FIG. 9
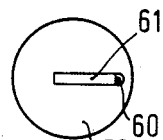
FIG 10
FIG. 7
FIG. 8

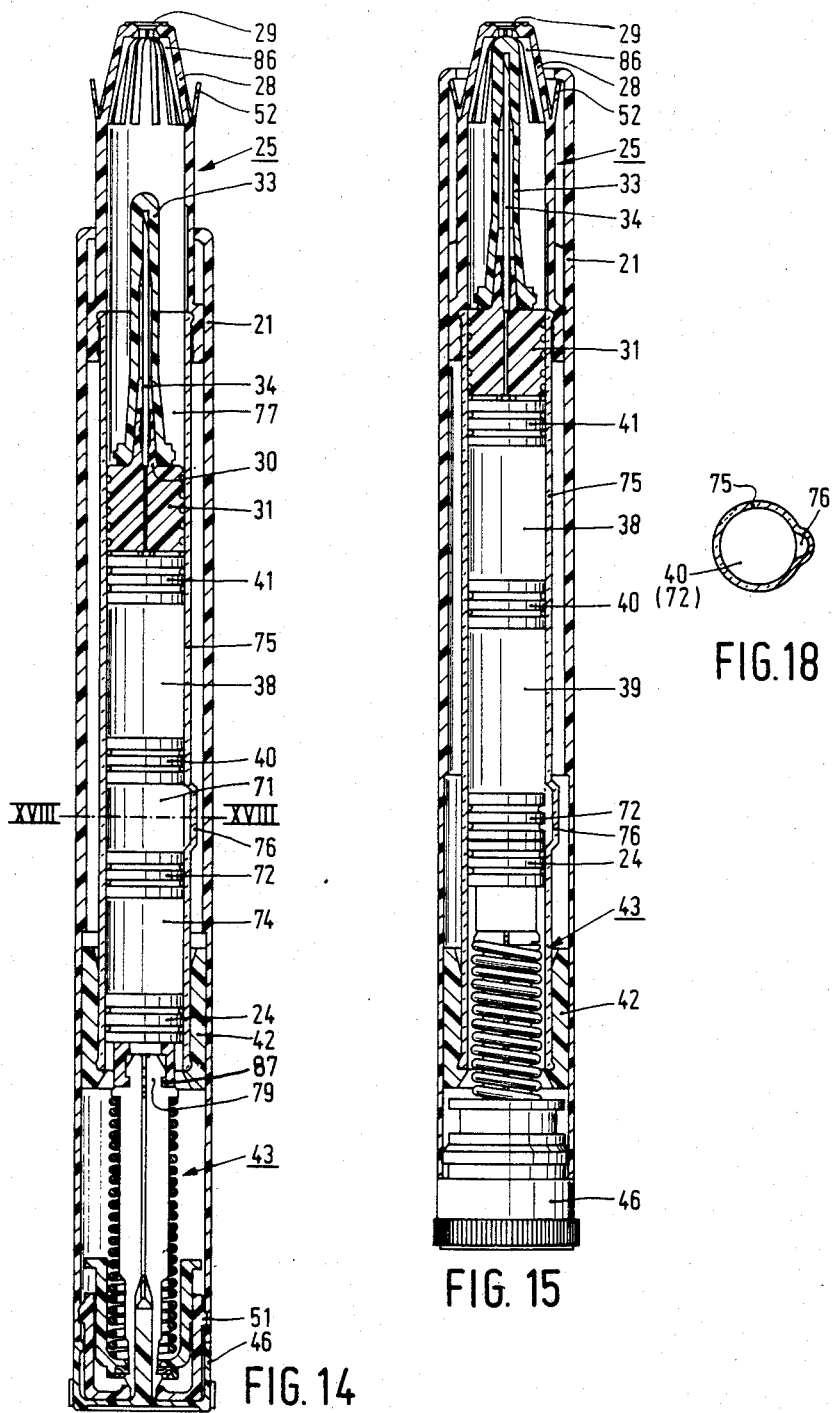

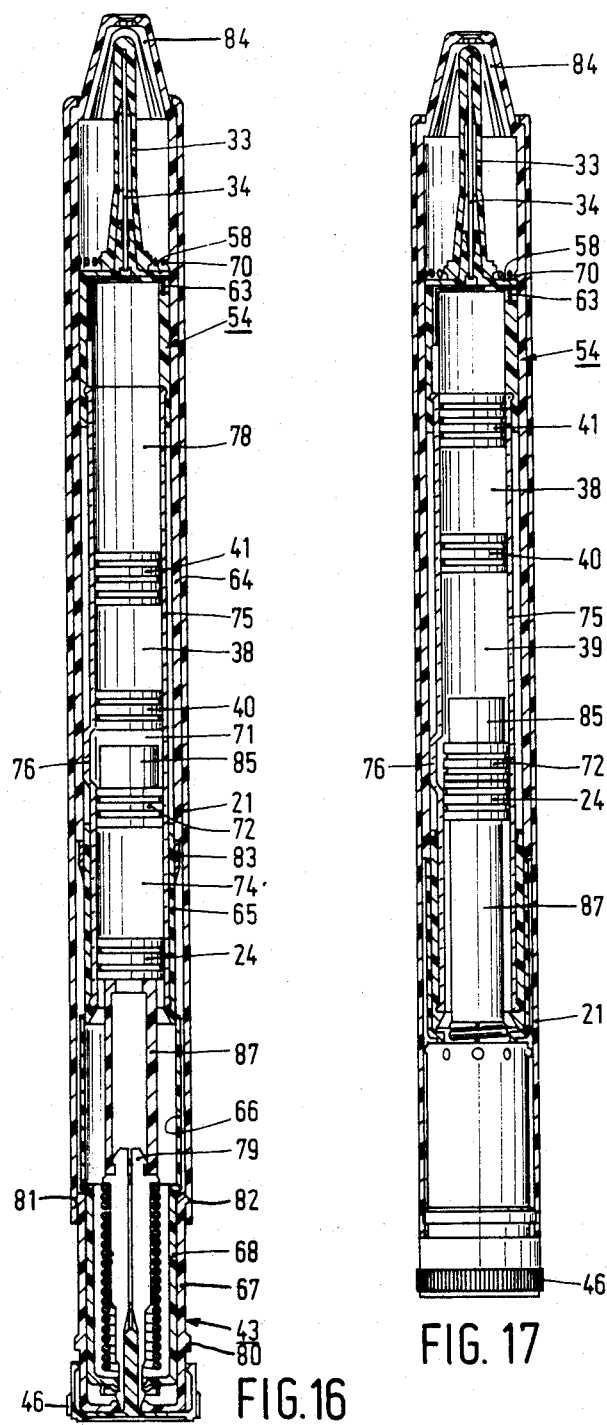

AUTOMATIC INJECTOR

BACKGROUND OF INVENTION

The present invention relates to an automatic injector for injecting one or more injection liquids.

Such an injector, viz. for injecting two or more different injection liquids, is known from U.S. Pat. No. 4,529,403. The injection needle of the injector described in that patent comprises a needle sheath of a flexible material that maintains the needle in a sterile condition during storage of the injector and serves as a shock absorber for the cartridge during operation of the injector. Such a needle guard is an excellent provision and is preferably also used in the injector according to the present invention.

Automatic injectors have been designed especially for use by human beings who have to administer an injection into their own body at a given instant that is not known beforehand. These persons include, for example, military persons exposed to an enemy's battle gas, for example, a nerve gas. Consequently, automatic injectors must satisfy stringent requirements regarding their reliability. Such injectors are usually stored for years at a time and in addition, after having been transferred to the potential users, are kept by those users for a long period of time under varying conditions. The proper operation of the injectors must be sufficiently ensured. At the critical instant, in fact, the lives of the users may depend on the operation of the injectors. Automatic injectors therefore must satisfy stringent requirements for storage stability. In particular, military authorities in various countries require a storage stability of at least five years, i.e. after five years of storage the automatic injectors must still operate reliably.

The injector described in U.S. Pat. No. 4,529,403, in particular the embodiment shown in FIGS. 1 and 2, has the disadvantage that during storage the foremost injection liquid, i.e. the injection liquid in front of the foremost separating stopper, is in constant contact with the synthetic material of the needle holder and with the metal of the injection needle. As a result of this, the application possibilities of the foremost compartment, i.e. the space in the needle holder, is restricted, because liquids present therein must be capable of withstanding contact with synthetic material and metals for at least five years. Of course, this is a restriction on the possible uses of the injector. An obvious solution, namely omit the injection liquid from the foremost compartment, in fact is not a solution. If such an injector were used, the air present in the foremost compartment would also be injected. This would be a severe disadvantage, because the air would enter the blood stream of the user and could cause an air embolism. It is therefore desirable to minimize the amount of air injected together with the injection liquid. One possibility for this purpose would be to reduce the length of the sealing stopper and hence the space in the needle holder. However, a thinner sealing stopper involves the risk of leakage and evaporation of the injection liquid, especially in the case of a required storage period of five years, so that a thinner stopper is not an acceptable solution to the problem.

SUMMARY OF THE INVENTION

It is an object of the present invention to provide an automatic injector that does not suffer the disadvantages discussed above and that maintains the advantages disclosed in U.S. Pat. No. 4,529,403, for example, easy handleability, readiness for rapid use, and the reliability resulting from a relatively uncomplicated design.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the automatic injector of the invention for injecting one or more injection liquids comprises:

a combination of a substantially cylindrical means containing a discharge mechanism and a plurality of cartridge elements, the cartridge elements comprising:

a piston that is movable in the substantially cylindrical means and seals same;

a sealing stopper that is movable in the substantially cylindrical means, whose circumference adjoins the inner wall of the cylindrical means in a sealing manner, and that, prior to use of the injector, seals the foremost injection liquid from the front end of the substantially cylindrical means;

a number of separating stoppers equal to one less than the number of the liquids, the separating stoppers being movable in the substantially cylindrical means and having circumferences that adjoin the inner wall of the cylindrical means in a sealing manner, thereby keeping the liquids separated from each other prior to use of the injector;

a needle holder comprising a neck for sealingly gripping a needle, and a needle holder stopper that is movable in the substantially cylindrical means, that at its rear end adjoins the front face of the sealing stopper, that at its front end adjoins the neck, that comprises a longitudinal bore that at the front end of the needle holder stopper communicates with the duct of the neck, and that comprises a by-pass means through which the one or more liquids behind the sealing stopper can reach the bore; and a needle sealingly gripped by the neck;

the substantially cylindrical means comprising:

a nose portion that tapers inwardly in the forward direction and terminates at its front end with an aperture to allow passage of the needle during operation of the injector and at its rear end comprises an abutment for the needle holder stopper in its ultimate forward position; and by-pass means in front of the sealing stopper for permitting the one or more liquids behind the sealing stopper to reach the needle holder by-pass means when during operation of the injector the sealing stopper and the number of separating stoppers are moved forward, the cylindrical means by-pass means extending in the longitudinal direction over a length that is substantially shorter than the combined lengths of the sealing stopper and the needle holder stopper;

wherein the substantially cylindrical means and the cartridge elements are so proportioned that when, during operation of the injector, the needle holder stopper has been moved forward, the needle holder stopper circumferentially adjoins in a sealing manner the inner wall of the substantially cylindrical means in front of the cylindrical means by-pass means, and that the distance between the rear end of the cylindrical means bypass means and the abutment for the needle holder stopper is slightly greater than the combined lengths of the needle holder stopper, the sealing stopper, and the separating stoppers, so that when all of the stoppers are in their ultimate forward positions, they do not cover the rear end of the cylindrical means by-pass means.

Since the invention includes an automatic injector for injecting a single injection liquid, "foremost injection liquid" as used herein should be understood to mean the only injection liquid as well as the injection liquid closest to the forward end in injectors for injecting a plurality of injection liquids.

Preferably, the substantially cylindrical means comprises a cartridge, a cartridge holder holding the cartridge, and an outer sleeve that can be moved telescopically around the cartridge holder. The cartridge preferably comprises a hollow, substantially cylindrical (which includes entirely cylindrical) barrel that is open at each end. The piston referred to above is movable in the barrel and seals the barrel, and the sealing and number of separating stoppers referred to above are movable in the barrel and have circumferences that adjoin the inner wall of the barrel in a sealing manner, the sealing stopper sealing the foremost injection liquid from the front end of the barrel. The cartridge holder preferably comprises a collar connected to the front end of the barrel in a sealing manner, the nose portion referred to above, and a hollow shaft between the collar and the nose portion having substantially the same inner diameter as the inner wall of the barrel. In this preferred embodiment, the cylindrical means by-pass means is in the wall of the hollow shaft or in the wall of the barrel in front of the sealing stopper.

The end abutment for the needle holder stopper in the cartridge holder nose portion may be formed, for example, by one or more inwardly projecting abutment cams or ridges provided on the inner wall of the nose portion.

The injector according to the present invention is particularly flexible because any desired number of injection liquids can be acccommodated therein by an unrestricted selection of the number of separating stoppers, of a cartridge holder with adapted shaft- and by-pass length, and of the length of the needle holder stopper. It is preferable for practical considerations to restrict the number of injection liquids to at most four.

Additional features that can be provided in preferred embodiments according to the invention broadly described above include the sealing stopper and the needle holder comprising a single unitary structure; a sheath means on the needle to maintain the needle in a sterile condition; the needle holder comprising a resilient material; and a bacteria filter provided in the aperture.

In a preferred embodiment the needle holder is constructed in such a way that the longitudinal bore of the needle holder stopper at the rear end adjoins the by-pass in the wall of the cartridge holder shaft or of the barrel via at least one slot radially recessed in the rear face of the stopper and an adjoining circumferential slot recessed in the same face at the circumferential edge. These slots constitute a preferred needle holder stopper by-pass means through which the injection liquids behind the sealing stopper can reach the bore. The needle holder may be manufactured, for example, by injection molding from a synthetic material suitable for that purpose.

The cartridge holder is preferably manufactured also by injection molding from a non-deformable, slightly resilient synthetic material. If the by-pass is provided in the wall of the cartridge holder shaft, this may be realized in various manners. The by-pass is preferably constructed so as to include at least one slot that is recessed in the inner wall of the shaft and that extends in the longitudinal direction of the shaft over a length that is substantially shorter than the combined lengths of the sealing stopper and the needle holder stopper. If the by-pass is provided in the barrel wall, it preferably consists of at least one outwardly projecting bulge of the barrel wall extending in the longitudinal direction of the barrel. In another preferred embodiment, the inner wall of the cartridge holder shaft or of the barrel at the area of the by-pass comprises at least one ridge that extends in the longitudinal direction of the shaft over a length that is substantially shorter than the combined lengths of the sealing stopper and the needle holder stopper so that during operation of the injector, these stoppers are deformed by contacting the ridge or ridges, a by-pass for the injection liquid or liquids being formed behind the stoppers through which the liquid or liquids can pass the stoppers. In still another preferred embodiment, the wall of the cartridge holder shaft or of the barrel at the area of the by-pass has an oval cross-section over a length that is substantially shorter than the combined lengths of the sealing stopper and the needle holder stopper. Of course, other constructions of the by-pass are feasible within the scope of the present invention.

The favorable properties of the injector according to the present invention will be apparent from the description of the operation of the injector. Because in the description below the operation of the injector according to the invention will be described in greater detail, a brief explanation will suffice here. When the injector is actuated, the piston and hence the contents of the barrel move forward in the barrel under the influence of a spring that as a power source forms part of the discharge mechanism. The needle holder with needle adjoining the sealing stopper also moves forward. The preferred flexible needle guard, if present, is compressed between the needle holder and the front end of the nose portion of the cartridge holder, and the injection needle pierces the closed end of the needle guard, emanates through the aperture or through a preferred filter in the aperture of the nose portion of the cartridge holder, if present, and enters into the body of the user in the place where the injection will be administered. The air present in the cartridge holder can escape via the aperture in the nose portion of the cartridge holder. At the instant the sealing stopper has moved forward sufficiently far into the shaft of the cartridge holder or in the barrel so that the entrance to the by-pass in the wall of the cartridge holder shaft or in the barrel wall is uncovered, the injection liquid can reach the injection needle via that by-pass and the by-pass in the needle holder stopper, and can be injected. Simultaneously, the needle holder stopper then has been moved forward over such a distance that a circumferential sealing is obtained so that the injection liquid cannot reach the space in front of the needle holder stopper and consequently also cannot reach the aperture in the nose portion of the cartridge holder. In the presence of more injection liquids, the injection liquid behind the separating stopper or stoppers is injected in the same manner after the liquid between the sealing stopper and the separating stopper or front separating stopper has left the injector. The sealing stopper is then pushed further forward by the separating stopper under the influence of the spring, and the air in the cartridge holder in front of the needle holder can further escape through the aperture in the nose portion. When the collective stoppers have been moved forward sufficiently far, the entrance to the by-pass in the wall of the cartridge holder shaft or of the barrel is uncovered for the injection liquid behind the separating stopper, as a result of which the injection liquid can be injected. At that instant the injection needle is in its foremost position, the needle holder being stopped by the end abutment in the narrowed nose portion of the cartridge holder.

The aperture in the nose portion of the cartridge holder must be sufficiently wide not only to allow passage of the injection needle but also to allow escape of the air from the space in the cartridge holder in front of the needle holder stopper without the possibility of excessive pressure build-up in that space. The aperture preferably comprises a bacteria filter to avoid contamination of the interior of the injector.

An additional advantage of the above-described injector over that of the previously mentioned U.S. Pat. No. 4,529,403 is that, when the injector according to the invention is actuated, the cartridge, which usually includes a glass barrel, is no longer pushed forward by the spring so that the possibility of glass fracture is reduced.

Further to achieve the foregoing objects and in accordance with the purpose of the invention, as embodied and broadly described herein, the automatic injector of the invention for injecting one or more injection liquids comprises:

a combination of a discharge mechanism, a cartridge holder, and a cartridge that is slidably positioned in the cartridge holder, the cartridge comprising:

a hollow, substantially cylindrical (which includes entirely cylindrical) barrel that is open at each end;

a piston that is movable in the barrel and seals same;

a sealing stopper that is movable in the barrel, whose circumference sealingly adjoins the inner wall of the barrel, and that, prior to use of the injector, seals the foremost injection liquid from the front end of the barrel;

a number of separating stoppers equal to one less than the number of liquids, the separating stoppers being movable in the barrel and having circumferences that adjoin the inner wall of the barrel in a sealing manner, thereby keeping the liquids separated from each other in the barrel prior to use of the injector;

a needle holder comprising:
(i) a collar connected to the front end of the barrel in a sealing manner:
(ii) a neck for sealingly gripping a needle;
(iii) a hollow, substantially cylindrical shaft between the collar and the neck;
(iv) a by-pass in the wall of the shaft, through which the one or more liquids behind the sealing stopper can reach the injection needle when during operation of the injector the stopper or stoppers is or are moved forward into the shaft of the needle holder, the by-pass comprising at least one duct recessed in the wall of the shaft and communicating the space in the shaft bounded by the inner wall of the shaft and the rear face of the neck with the neck aperture of the needle holder, the duct, from approximately the rear edge of the shaft over a part of the length of the shaft substantially shorter than the length of the sealing stopper, being in open communication with the space in the shaft, but for the remaining part being separated from the space; and (v) at the front end of the shaft, at least one aperture recessed in the wall of the shaft, the aperture communicating the space in the shaft with the interior of the cartridge holder; and a needle sealingly gripped by the neck;

wherein the shaft is so proportioned that the space bounded by the inner wall of the shaft and the rear face of the neck, apart from the by-pass, has approximately the same diameter as the inner wall of the barrel and is slightly longer than the combined lengths of the sealing stopper and the number of separating stoppers, so that the sealing and separating stoppers in the ultimate forward position can fill the space substantially entirely but do not cover the end of the by-pass adjoining the barrel.

In this embodiment the injector according to the present invention is also particularly flexible because any desired number of injection liquids can be accommodated therein by selecting the number of separating stoppers, a needle holder with adapted shaft length, and the length of the sealing stopper. For practical reasons, it is desirable to restrict the number of injection liquids to at most four.

Additional features that can be provided in preferred embodiments according to this embodiment of the invention, as broadly described above, include an outer sleeve that can be moved telescopically around the cartridge holder; the needle being covered by a sheath to maintain the needle in a sterile condition; and the at least one aperture recessed in the wall of the shaft comprising a bacteria filter.

From the point of view of technical manufacturing, it is preferred (1) that the needle holder comprise two portions, the first portion comprising the collar and the shaft, the other portion comprising the neck, the shaft being closed at its front end by means of an end wall and the by-pass in the wall of the shaft being formed by at least one duct recessed in the side wall of the shaft and extending in the longitudinal direction thereof, the duct communicating with at least one slot radially recessed in the front face of the end wall, and the neck portion of the needle holder comprising a flange having an approximately equally large diameter as the end wall of the shaft, by means of which flange the neck portion at its circumferential edge is sealingly connected to the front face of the end wall of the shaft in such a way that the neck aperture communicates with the slot or slots recessed in the front end wall; and (2) that the aperture in the wall of the shaft be recessed in the front end of the side wall or where the side wall and the end wall adjoin each other.

The needle holder is preferably manufactured by injection molding from a non-deformable, slightly resilient synthetic material.

The favorable properties of the injector according to the present invention in this latter embodiment also will be apparent from the detailed description below of the operation of the injector. In this case also a brief explanation will suffice here. When the injector is actuated, the cartridge moves forward in the cartridge holder under the influence of a spring that as a power source forms part of the discharge mechanism. The needle guard is compressed, the injection needle piercing the closed end of the needle guard, emanating to the exterior through an aperture recessed in the front end of the cartridge holder, and entering into the body of the user in that place where the injection will be administered.

When the needle has entered into the body of the user, the forward movement of the piston begins under the influence of the same spring. The pressure on the piston propagates via the injection liquids and separating stopper or stoppers on the sealing stopper. As a result of this the sealing stopper is moved forward into the shaft of the needle holder. The air present in the shaft in front of the sealing stopper escapes via the aperture in the wall of the shaft and can thus escape because the interior of the cartridge holder is in open communication with the atmosphere. When the sealing stopper has moved forward sufficiently far into the shaft of the needle holder, the entrance to the duct in the wall of the shaft is uncovered for injection liquid, so that the injection liquid can reach the injection needle via this duct and can be injected. Simultaneously, the sealing stopper has then been moved forward into the shaft over such a distance that a circumferential sealing is obtained between the front end of the stopper and the shaft so that the injection liquid cannot reach the space in front of the sealing stopper and consequently also not the aperture in the wall of the shaft. In the presence of more injection liquids, the injection liquid behind the separating stopper or stoppers is injected in the same manner after the liquid between the sealing stopper and the separating stopper or front separating stopper has left the injector. The sealing stopper is then pushed further forward into the shaft of the needle holder by the separating stopper, the air in the shaft in front of the sealing stopper further being able to escape. When the collective stoppers have been moved forward sufficiently far, the entrance to the duct in the wall of the shaft is uncovered for the injection liquid behind the separating stopper, as a result of which the injection liquid can be injected. This continues automatically until all the injection liquid has been injected. At that instant the injection needle is in its foremost position, the needle holder being stopped by a narrowed nose portion at the front end of the cartridge holder and/or by the needle guard compressed between the needle holder neck and the end of the nose portion.

The aperture in the wall of the shaft of the needle holder must be sufficiently wide to allow easy escape of the air from the space in front of the sealing stopper without the possibility of excessive pressure build-up in the space. The aperture optionally comprises a bacteria filter to avoid contamination of the interior of the injector.

The administration of several medicaments or antidotes is often necessary in particular in military applications, inter alia because, of course, the nature and composition of the battle gas used by the enemy are not known in advance, and/or to achieve an effective therapy. The injector in accordance with the present invention therefore is extremely suitable for accommodating such medicaments if they are not compatible with each other during a long period of storage. Some medicaments that are sufficiently storage-stable, such as solids, are not stable during the required long period of storage after having been dissolved in a solvent to form a composition suitable for injection. An injector in which a solid as such can be accommodated might provide a solution to the problem of storing these medicaments. Such an automatic injector, however, has not yet been realized. Obviously the technical problems occurring in developing such an injector have been prohibitive.

The present invention also provides a solution to the above problem, starting with the recognition that the instability of such medicament solutions is always relative, i.e. that such substances always have some stability, albeit small, in solution. The injector according to the present invention can extremely suitably be used for the separate storage of at least two different substances that must not be in contact with each other for a long period of time, one of the substances in the injector being solid that can be injected as an injection liquid only after dissolving in a solvent. This can be done if the injector is made ready for use by a simple operation before the actual use. This simple operation of making the injector ready for use may be carried out a shorter or longer time before the use of the injector, depending on the stability of the medicament solution, either by the potential user him or herself, or by the person who transfers the injector to the user. In order to minimize the possibility of mistakes, it is preferable to make the injector ready for use immediately before or upon providing the injector to the potential users, for example, soldiers in the field. This is advisable in all those cases in which the medicaments or antidotes in solution are sufficiently stable for a period of at least a few hours or days.

Making the injector ready for use is a simple operation, namely a simple telescoping movement of external parts of the injector with respect to each other, which can easily be carried out in a dust-free package, for example, a flexible blister pack. Since it is not necessary to remove the package for making the injector ready for use, the risk is avoided that the safety member might inadvertently be removed, as a result of which the injector might prematurely, i.e. before the intended use, be discharged. Moreover, the reliability of the injector is maintained since no dust particles or other contaminants can reach the injector. The user should open the package only for the actual use, after which the safety member can be removed and the injector can be used for the administration of an injection.

In order to be able to use the injector of the former embodiment—namely the construction in which the by-pass for injection liquid is in the substantially cylindrical means, preferably in the cartridge holder shaft or in the barrel, and the needle holder is movable in the barrel—for the separate storage of at least two different substances one of which is a solid that can be injected as an injection liquid only after dissolution in a solvent, the substantially cylindrical means of the injector according to a preferred embodiment of the present invention comprises means containing the cartridge elements and an outer sleeve, the discharge mechanism being in operative relationship to the piston via a plunger and capable of telescoping movement relative to the means containing the cartridge elements, whereby the contents of the means containing the cartridge elements, including the needle holder with the needle, can be moved forward in the means containing the cartridge elements, as a result of which the injector is made ready for use;

the injector further comprising:

between the piston and the sealing stopper a passable stopper that is movable in the means containing the cartridge elements and that prior to making the injector ready for use adjoins the inner wall of the means containing the cartridge elements in a circumferentially sealing manner and keeps the solid separated from the solvent;

a solvent by-pass means for liquid in the wall of the means containing the cartridge elements, the solvent by-pass means being slightly longer than the passable stopper and, when the injector is made ready for use, permitting the solvent to pass the passable stopper and reach the solid in front of the passable stopper and dissolve same, but the solvent by-pass means, prior to making the injector ready for use, being sealed from the solvent present behind the passable stopper by means of the passable stopper; and prior to making the injector ready for use, a space that is not filled with substance and that on its rear and lateral sides is bounded by the front of the needle holder stopper and the inner wall of the means containing the cartridge elements, the empty space being so proportioned that the distance between the front end of the injection needle and the aperture in the nose portion is at least as long as the distance from the front face of the piston or, in the presence of a separating stopper behind the passable stopper, of the separating stopper to the rear end of the solvent by-pass means.

The above expression "a solid that can be injected as an injection liquid only after dissolution in a solvent" also includes a medicament that can be injected as an injection liquid only after dilution with a diluent. Such medicaments may be in the form of pastes or concentrated solutions that cannot be injected as such. The "solvent by-pass means" then serves as a by-pass means for the diluent. Consequently, the terms "solid" and "solvent" as used herein should be understood to include a "medicament to be diluted before injection" and a "diluent" for such a medicament.

In this preferred embodiment, the means containing the cartridge elements preferably comprises a cartridge and a cartridge holder holding the cartridge, the cartridge comprising:

a hollow, substantially cylindrical (which includes entirely cylindrical) barrel that is open at each end; wherein the piston is movable in the barrel and seals the barrel; and the sealing, number of separating, and passable stoppers are movable in the barrel and have circumferences that adjoin the inner wall of the barrel in a sealing manner, the sealing stopper sealing the foremost injection liquid from the front end of the barrel;

the cartridge holder comprising:

a collar connected to the front end of the barrel in a sealing manner;

the nose portion; and a hollow shaft between the collar and the nose portion having substantially the same inner diameter as the inner wall of the barrel;

wherein the cylindrical means by-pass means is in the wall of the shaft or in the wall of the barrel in front of the sealing stopper, and wherein the empty space is bounded on its lateral sides by the inner wall of the barrel, the empty space in the barrel through which the injection needle extends being at least as long as the distance from the front face of the piston or, in the presence of a separating stopper behind the passable stopper, of the separating stopper to the rear end of the solvent by-pass means.

In one such embodiment the outer sleeve may be capable of telescoping movement around the cartridge holder, and the discharge mechanism may be rigidly connected to the outer sleeve. Alternatively, the outer sleeve may be telescopically connected to the discharge mechanism. The term "discharge mechanism" as used herein should be understood to include a functional part of the discharge mechanism, e.g. a safety member as defined hereinafter.

The solid may be present in the form of an, optionally lyophilized, powder, a tablet, granules, crystals, pills, and the like.

If the injector comprises, in addition to a solid and a solvent therefor, one or more injection liquids, these may be situated in front of or behind the compartments containing solid and solvent. In the former case, which is preferred for practical reasons, the solid is enclosed between the passable stopper and the separating stopper or the rear separating stopper, and the solvent for the solid between the piston and the passable stopper. In the latter case, the solvent for the solid is enclosed between a separating stopper and the passable stopper, while behind the separating stopper injection liquid is provided in the injector.

An essential aspect of this embodiment of the invention is the empty space in the barrel in front of the needle holder stopper, in which, when the injector is made ready for use, the needle holder with needle can move forward. The air present in this space can escape freely via the aperture in the nose portion of the cartridge holder, which preferably comprises a bacteria filter.

The injector preferably comprises an indication that the injector is ready for use, so that the user can easily ascertain that the operation of making the injector ready for use has been carried out. A good indication is, for example, the provision of a conspicuous color (signal color) on that portion of the cartridge holder that slides into the outer sleeve when the injector is made ready for use.

Due to the simplicity of the operation for making the injector ready for use, the injector according to this preferred embodiment of the present invention is also particularly suitable for packaging in a multi-unit pack, for example, a multi-unit box, in which, when the injectors are transferred to the potential users, the injectors can be made ready for use collectively, for example, by telescoping movement of a wall of the box.

It is further preferred, in the embodiment in which the outer sleeve is capable of telescoping movement around the cartridge holder, and the discharge mechanism is rigidly connected to the outer sleeve, after making the injector ready for use and certainly when using the injector, to prevent the cartridge holder with the cartridge from emanating forward from the outer sleeve. Therefore, means are preferably provided to lock the cartridge holder in the outer sleeve after having made the injector ready for use. Suitable locking means comprise a plurality of outwardly projecting resilient lug-shaped elements or catches engaging behind an inwardly bent edge at the front end of the outer sleeve and thus preventing a forward movement of the cartridge holder in the outer sleeve, the elements or catches being connected at one end to the outer wall of the cartridge holder and otherwise being directed forward and standing free from the cartridge holder at an acute angle with the cartridge holder wall.

In the embodiment in which the outer sleeve is telescopically connected to the discharge mechanism, suitable means for locking the cartridge in the cartridge holder while making the injector ready for use comprise, for example, a plurality of resilient abutting cams connected to a sleeve clamped around the rear end of the barrel, which cams engage the rear edge of the cartridge holder and which, when the injector has been made ready for use, are unlocked by a force directed against the resilience of the abutting cams.

In the embodiment in which the outer sleeve is telescopically connected to the discharge mechanism, it is also preferable, after making the injector ready for use, to lock the discharge mechanism in the outer sleeve. When a discharge mechanism is used as described in outline of U.S. Pat. No. 4,529,403 cited above, namely which comprises a coil spring as a power source the rear end of which is accommodated in an inner pistol sleeve that is slidably provided in an outer pistol sleeve, a good locking can be obtained by providing the rear end of the outer sleeve around the outer pistol sleeve so as to be telescopically slidable and by providing the components with means to lock the outer pistol sleeve in the outer sleeve after having made the injector ready for use. The locking means preferably comprises a radially outwardly projecting circumferential ridge or a plurality of radially located cams on the outer wall of the outer pistol sleeve, which ridge or which number of cams engages in a circumferential groove in the inner wall of the rear end of the outer sleeve.

In order to be able to use the injector of the second embodiment, i.e. in the embodiment having the by-pass for injection liquid in the shaft of the needle holder, for the separate storage of at least two different substances one of which is a solid that can be injected as an injection liquid only after dissolving in a solvent, the injector of this latter embodiment according to the present invention is constructed in such a way that the discharge mechanism is in operative relationship to the piston via a plunger and is capable of telescoping movement relative to the cartridge holder, whereby the contents of the barrel can be moved forward in the barrel so that the injector is made ready for use;

the injector further comprising:

between the piston and the sealing stopper a passable stopper that is movable in the barrel and that prior to making the injector ready for use adjoins the inner wall of the barrel in a circumferentially sealing manner and keeps the solid separated from the solvent;

solvent by-pass means for liquid in the wall of the barrel, the solvent by-pass means being slightly longer than the passable stopper and, when the injector is made ready for use, permitting the solvent to pass the passable stopper and reach the solid in front of the passable stopper and dissolve same, but the solvent by-pass means, prior to making the injector ready for use, being sealed from the solvent present behind the passable stopper by means of the passable stopper;

prior to making the injector ready for use, a space that is not filled with substance and that is bounded on its rear and lateral sides by the front face of the sealing stopper and the inner wall of the barrel, and that on its front side is in open communication with the space in the shaft of the needle holder, the empty space in the barrel being at least as long as the distance from the front face of the piston or, in the presence of a separating stopper behind the passable stopper, of the separating stopper to the rear end of the solvent by-pass means; and means for preventing the cartridge in the cartridge holder from moving forward when the injector is made ready for use.

In this embodiment also, the outer sleeve may be capable of telescoping movement around the cartridge holder, and the discharge mechanism may be rigidly connected to the outer sleeve; or alternatively the outer sleeve may be telescopically connected to the discharge mechanism. For each of these alternatives, the same respective means recited above to prevent the cartridge holder with the cartridge from emanating forward from the outer sleeve, to lock the cartridge in the cartridge holder, and to lock the discharge mechanism in the outer sleeve may be provided.

In this embodiment also, one or more injection liquids, in addition to a solid and a solvent therefor, may be accommodated in the injector, if desired, in front of or behind the compartments with solid and solvent.

An essential aspect of the invention again is the empty space in front of the sealing stopper in which, when the injector is made ready for use, in the last-mentioned embodiment the sealing stopper can move forward. The air present in the space can freely escape via the aperture in the wall of the needle holder shaft, which optionally comprises a bacteria filter.

In this latter embodiment also a good indicator for the ready-for-use condition may be desirable, for example, a conspicuous color provided on that portion of the outer pistol sleeve that slides into the outer sleeve when the injector is made ready for use.

In this embodiment also, it is possible to collectively make a large number of injectors ready for use in a multi-unit pack in a simple manner, as indicated above. As will be apparent, various components of the embodiments of the injection according to the present invention, for example, outer sleeve, cartridge holder, and pistol sleeves, are preferably manufactured from a nondeformable, slightly resilient synthetic material, preferably by injection-molding.

In order to reduce the amount of air in the compartment of the injector in which the solid is accommodated, it may be advantageous to lengthen the front of the passable stopper and/or the rear of the sealing stopper or separating stopper by a cylindrical part of reduced diameter, or to provided a molded member of an inert material in this compartment. As a result of this, the volume of the space in the barrel provided for the solid is reduced.

The solvent by-pass means in the barrel wall can be constructed in various manners. The barrel may be made of glass or of a suitable synthetic material; in the latter case the barrel may be manufactured, for example, by injection molding. When the barrel is of synthetic material, the by-pass in the barrel wall preferably comprises at least one slot recessed in the inner wall of the barrel and extending in the longitudinal direction of the barrel over a length that slightly exceeds the length of the passable stopper. In another preferred embodiment, the inner wall of the barrel at the area of the by-pass comprises at least one ridge that extends in the longitudinal direction of the barrel over a length that slightly exceeds the length of the passable stopper so that, when the injector is made ready for use, the stopper is deformed by contact with the ridge or ridges, a by-pass for the solvent behind the passable stopper being formed, through which the liquid can pass the stopper. Similar by-passes can also be provided in a glass barrel wall, but synthetic materials are better suitable for this purpose. A barrel of glass is by far to be preferred to a synthetic material barrel because synthetic materials generally are less suitable than glass to store liquids for a long period of time that are to be injected; synthetic materials may contaminate the liquids or influence the stability of the liquids adversely. The disadvantage of glass, however, is that it is fragile. If a barrel of unhardened glass is used, a sheath of plastic sheet, shrunk around the barrel, may advantageously be applied, as disclosed in U.S. Pat. No.

4,565,543, preferably as shown in FIG. 4 of that patent. In a glass barrel, the barrel wall can most simply be provided with a by-pass by deforming the wall of the barrel at the area of the by-pass over a length that slightly exceeds the length of the passable stopper so that, when the injector is made ready for use, the solvent behind the stopper can pass the stopper at the area of the deformation. The local deformation of the barrel wall preferably comprises at least one outwardly projecting longitudinal bulge of the barrel wall through which, when the injector is made ready for use, the solvent behind the passable stopper can reach the solid in front of the stopper, or comprises at least one inwardly projecting longitudinal ridge of the barrel wall, by which, when the injector is made ready for use, the passable stopper is deformed by contact with the ridge or ridges, a by-pass for the solvent behind the passable stopper being formed through which the liquid can reach along the stopper the solid in front of the stopper. The barrel wall may alternatively be deformed locally in such a manner that the barrel wall at that area has an oval cross-section through which, when the injector is made ready for use, the solvent behind the passable stopper can reach the solid in front of the stopper.

A local deformation of the wall of the barrel in the form of one or more outwardly projecting longitudinal bulges is generally considered to be the best suitable solution for a by-pass in the glass barrel wall because it can very simply be provided in a barrel wall and during operation of the injector constitutes a reliable by-pass for the solvent. The collared cartridge holder or needle holder, together with the clamping sleeve connected in a clamping manner around the rear end of the barrel and to be described below, ensures that such a bulge or such bulges in the glass barrel wall is/are protected from damage or fracture during assembly of the injector. By using a collared cartridge holder or needle holder and a clamping sleeve, it is moreover not necessary to adapt the shape of the outer sleeve or cartridge holder to the shape of the outwardly bent by-pass in the barrel and the assembling, and in particular the automatic assembling, of the cartridge in the holder or outer sleeve is not hampered by the non-symmetric cross-section of the barrel at the area of the by-pass.

The accompanying drawings, which are incorporated in and constitute a part of this specification, illustrate several preferred embodiments of the invention and, together with the description, serve to explain the principles of the invention.

BRIEF DESCRIPTION OF THE DRAWINGS

FIGS. 4, 5, and 6 illustrate the operation of the injector shown in FIG. 1, in which the injector is shown partly in a side elevation and partly in a longitudinal sectional view;

FIG. 7 is a longitudinal sectional view of the injector shown in FIG. 1, this time with one injection liquid;

FIG. 8 is a longitudinal sectional view of an injector in accordance with the present invention in another embodiment, in the condition in which it can be transported and stored;

FIG. 9 is a cross-sectional view through the needle holder of the FIG. 8 injector, at the area of the needle holder shaft, taken on the line IX—IX viewed in the direction of the injection needle;

FIG. 10 is a top view of the needle holder shaft at the area of the connection of the flange of the neck portion of the needle holder to the needle holder shaft, viewed in the direction of the barrel;

FIGS. 14 and 16 and longitudinal sectional views of two other embodiments of injectors in accordance with the present invention, both suitable for accommodating a solid;

FIGS. 15 and 17 show the injectors of FIGS. 14 and 16, respectively, this time at the instant at which they are ready for use; and FIG. 18 is a cross-sectional view through the barrel of the injector shown in FIG. 14 at the area of the by-pass in the barrel, namely taken on the line XVIII—XVIII, viewed in the direction of the needle or of the discharge mechanism.

DESCRIPTION OF THE PREFERRED EMBODIMENTS

Reference will now be made in detail to the presently preferred embodiments of the invention, examples of which are illustrated in the accompanying drawings.

Figure 1:
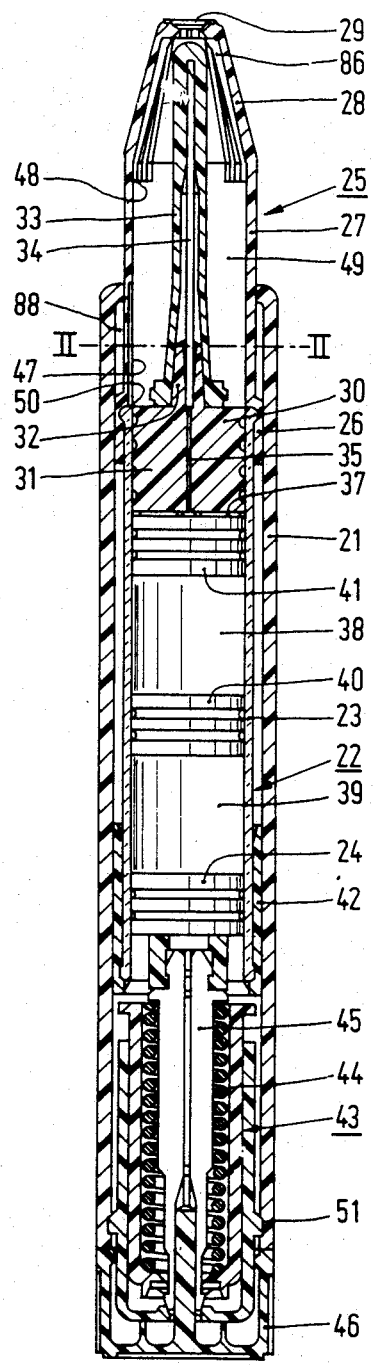
FIG. 1 is a longitudinal sectional view of an injector according to the present invention, in which two injection liquids are accommodated, in the position in which it can be transported and stored.
Figure 2:
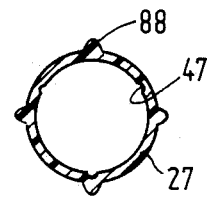
FIG. 2 is a cross-sectional view through the cartridge holder of the FIG. 1 injector, taken on the line II—II.
Figure 3:
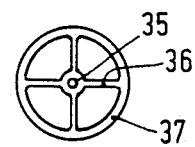
FIG. 3 is a bottom view of the needle holder stopper, viewed in the direction of the needle.

The injector shown in FIGS. 1-3 is constructed for the greater part as described in U.S. Pat. No. 4,529,403 cited above and in Netherlands Patent Specification No. 160,725. In outline, the injector comprises a cylindrical outer sleeve 21, in which a cartridge assembly 22 is slidably accommodated, comprising a cylindrical glass barrel 23 with injection liquids, a piston 24 in one end of the barrel, and a cartridge holder 25 at the other end. At each end the barrel comprises a radially outwardly projecting flange around which, on the side of the cartridge holder, the cartridge holder is connected by means of a collar 26. The cartridge holder furthermore comprises a shaft 27 that is cylindrical for the greater part, and a tapering nose portion 28 that has an aperture 29 at its front end. This aperture comprises a pierceable bacterial filter. Furthermore, accommodated in the barrel is a needle holder 30, like the piston manufactured from a resilient material, for example, an elastic synthetic material. The needle holder comprises a stopper 31 that is movable in the barrel and a neck 32 at the front end of the stopper that forms one assembly with the stopper. An injection needle 34 comprising a needle guard 33 is sealingly connected in the needle holder neck, for example, by gluing or clamping, or by means of so-called "insert-molding," in which the needle, simultaneously with the injection molding of the needle holder, is covered at the connection area with synthetic material. This latter connection is, of course, possible only if the needle holder can be manufactured by injection molding from a synthetic material suitable for this purpose. The needle holder stopper centrally comprises a longitudinal boring 35 that communicates at its front end with the neck aperture. As can best be seen in FIG. 3, the needle holder stopper comprises four slots 36 that are recessed in the rear face of the stopper and that communicate with a circumferential slot 37 recessed in the same face. The barrel 23 is internally divided into two separated liquid compartments 38 and 39 by means of a separating stopper 40, while the front compartment is closed by means of a sealing stopper 41. Separating stopper and sealing stopper are provided in the barrel so as to be movable and circumferentially sealing on the inner wall of the barrel and, like the piston, are manufactured from a resilient material, preferably rubber of a pharmaceutical quality. The front face of the sealing stopper engages the rear face of the needle holder stopper. An externally cylindrical clamping sleeve 42 is connected around the flange at the rear end of the barrel and at its rear end internally comprises a circumferential groove and a circumferential radially inwardly projecting edge for a clamping connection to the end of the barrel. The clamping sleeve externally adjoins the inner wall of the outer sleeve 21. The cartridge assembly 22 is provided in the outer sleeve 21 in such manner that the closed end of the needle guard 33 bears against a plurality of longitudinal ridges 86 on the inner wall of the nose portion 28 of cartridge holder 25, the nose portion comprising aperture 29. The rear ends 48 of the longitudinal ridges 86 constitute an abutment for the needle holder stopper when the stopper is in its ultimate forward position. The outer sleeve has such a length that in one end the cartridge assembly 22 is accommodated and in the other end the discharge mechanism 43. The discharge mechanism is locked in the outer sleeve by means of a radially outwardly projecting edge 51 that engages in a groove in the inner wall of the outer sleeve. The cartridge holder is locked against forward sliding movement by means of a plurality of longitudinal ridges 88 the front ends of which engage an inwardly bent edge at the front end of the outer sleeve. The discharge mechanism, which comprises a coil spring 44 as a power source, in outline is the same as the discharge mechanism described in the above-mentioned Netherlands Patent Specification No. 160,725, and comprises a locking mechanism 45 and a safety member 46. In the inner wall of the cartridge holder shaft 27, three longitudinal slots 47 are recessed that extend from the rear end of the shaft forward over a length that is substantially shorter than the length of the sealing stopper and needle holder stopper collectively. Furthermore, the shaft 27 of the cartridge holder is proportioned in such a way that the space 49 bounded by the inner wall of the shaft and the end abutment 48 for the needle holder stopper, apart from the slots in the shaft, has approximately the same diameter as the inner wall of the barrel 23 and is slightly longer than the needle holder stopper 31 together with the sealing stopper 41 and the separating stopper 40, so that in its ultimate forward position, the space 49 can be filled substantially entirely by the collective stoppers; however, the ends 50 of the slots adjoining the barrel remain uncovered.

When using the injector shown in FIGS. 1-3, first the safety member 46 is removed, after which the locking mechanism is unlocked by pressing the nose portion 28 of the cartridge holder against the body in the place where the injection is to be administered. The unlocking of the discharge mechanism takes place by the rearward movement of the cartridge holder 25 in the outer sleeve 21. When the injector is actuated, as is shown in FIGS. 4, 5, and 6, the piston, stoppers and injection liquids move forward in the barrel under the influence of the spring. The needle holder with injection needle 34 also moves forward, the resilient needle guard 33 being compressed between the needle holder and the front end of the longitudinal ridges 86 in the nose portion 28 of the cartridge holder. The needle pierces the closed end of the needle guard and emanates through the filter of the aperture 29 in the nose portion of the cartridge holder; the air present in front of the needle holder stopper in the cartridge holder can escape through the aperture 29. At the instant the sealing stopper 41, which engages the needle holder stopper, has been moved so far as is shown in FIG. 4, the entrance to the slots 47 in the wall of the shaft of the cartridge holder is uncovered for the injection liquid in compartment 38, so that this injection liquid can reach the boring in the needle holder stopper and hence the injection needle 34 via slots 47 and the slots 37 and 36 recessed in the rear face of the needle holder stopper, and can be injected. At the same time, as is also shown in FIG. 4, the needle holder has been moved forward into the shaft of the cartridge holder so far that the front end of the needle holder stopper adjoins the inner wall of the shaft in a circumferentially sealing manner and thus prevents the injection liquid from reaching the space in front of the needle holder stopper.

When all the liquid from compartment 38 has been injected, the front face of the separating stopper 40 engages the rear face of the sealing stopper 41. Under the influence of the coil spring 44, these stoppers, together with the needle holder stopper, are further pushed forward into the shaft of the cartridge holder, in which the air present in front of the stoppers can again escape via the aperture 29 in the nose portion 28. When the stoppers have occupied the position as shown in FIG. 5, the entrance to the slots 47 is uncovered for the injection liquid in compartment 39, which can then leave the injector in the same manner as the first injection liquid.

As will be obvious from a comparison of FIG. 4 and FIG. 5, the injection needle, upon expelling the injection liquid from compartment 39, has further emanated from the nose of the injector than upon expelling the injection liquid from compartment 38. This is advantageous because as a result of this, the total injection liquid is injected at different depths of the muscle tissue, which stimulates the take up of the liquid by the tissue. When all the injection liquid has been injected, the piston and stoppers engage each other, as is shown in FIG. 6. The needle holder with needle is now in its ultimate forward position, the needle holder being stopped by the rear ends 48 of the longitudinal ridges 86 in the nose portion 28 of the cartridge holder.

The injector shown in FIG. 7 is the same as that of FIG. 1, but this time filled with one injection liquid; corresponding components are referred to by the same reference numerals.

The injector shown in FIGS. 8-10 is also constructed for the greater part as is described in the above-mentioned U.S. Pat. No. 4,529,403 and the above-mentioned Netherlands Patent Specification No. 160,725. Components corresponding to those of FIGS. 1-3 are referred to by the same reference numerals, namely outer sleeve 21, barrel 23 with injection liquids, piston 24, needle guard 33, injection needle 34, liquid compartments 38 and 39, separating stopper 40, sealing stopper 41, discharge mechanism 43, coil spring 44, locking mechanism 45, and safety member 46. In the outer sleeve 21 is slidably accommodated a cartridge holder 64, in which is accommodated a cartridge assembly 53 comprising the barrel 23 with injection liquids, the piston 24 in one end of the barrel, and a needle holder 54 at the other end thereof. The needle holder is connected to the front end of the barrel by means of a collar 55. The needle holder furthermore comprises a neck 56 in which the injection needle 34 is connected, and a shaft 57 between collar and neck. The needle holder is manufactured from a synthetic material, namely in two portions: a neck portion with the neck 56 and a flange 58, and a portion comprising the collar 55 and the shaft 57. At its front the shaft is closed by an end wall 59, which on its front face is sealingly connected, for example by welding or luting, at the circumferential edge thereof to the flange 58 of the neck portion. A duct 60 is recessed in the side wall of the shaft and communicates with slot 61 recessed radially in the front face of the end wall, the slot communicating with the neck aperture. The duct 60 in the side wall of the shaft is partly, namely at 62, in open communication with the space in the shaft of the needle holder. The length of open communication 62 is substantially shorter than the length of the sealing stopper 41. In the front end of the shaft, an aperture 63, which preferably comprises a bacteria filter, is recessed in the wall of the shaft. A clamping sleeve 65, which is slidably accommodated in the cartridge holder, is clamped around the flange at the rear end of the barrel again by means of a snap connection. The cartridge assembly 53 is accommodated in the cartridge holder 64 in such a way that the closed end of the needle guard 33 engages the forward end of the tapering nose portion of the cartridge holder, which end comprises an aperture 69. A plurality of longitudinal ridges 84 in the nose portion ensure that during operation of the injector the aperture 69 cannot be sealed by the closed end of the needle guard. In order to prevent unintentional forward movement of the barrel with needle holder in the cartridge holder, the inner wall of the cartridge holder is provided with a number of radially positioned, radially inwardly projecting cams 70, which engage the front face of the flange 58 of the neck portion of the needle holder. The discharge mechanism 43 comprises a coil spring 44 as a power source, which is accommodated in the inner pistol sleeve 68, which is slidably accommodated in an outer pistol sleeve 67. The outer sleeve 21 is rigidly connected (locked) around the outer pistol sleeve by means of a radially outwardly projecting ridge 80 on the outer wall of the pistol sleeve, which ridge engages in a circumferential groove 82 in the inner wall of the rear end of the outer sleeve.

The shaft of the needle holder, not counting the duct 60 recessed in the wall, has an inside diameter that is approximately equal to that of the barrel. Furthermore, the shaft is slightly longer than the sealing stopper and the separating stopper together, so that the open part 62 of the duct 60 is uncovered when the stoppers have been moved into their ultimate forward position against the end wall 59 of the shaft.

Figures 11, 12, 13:
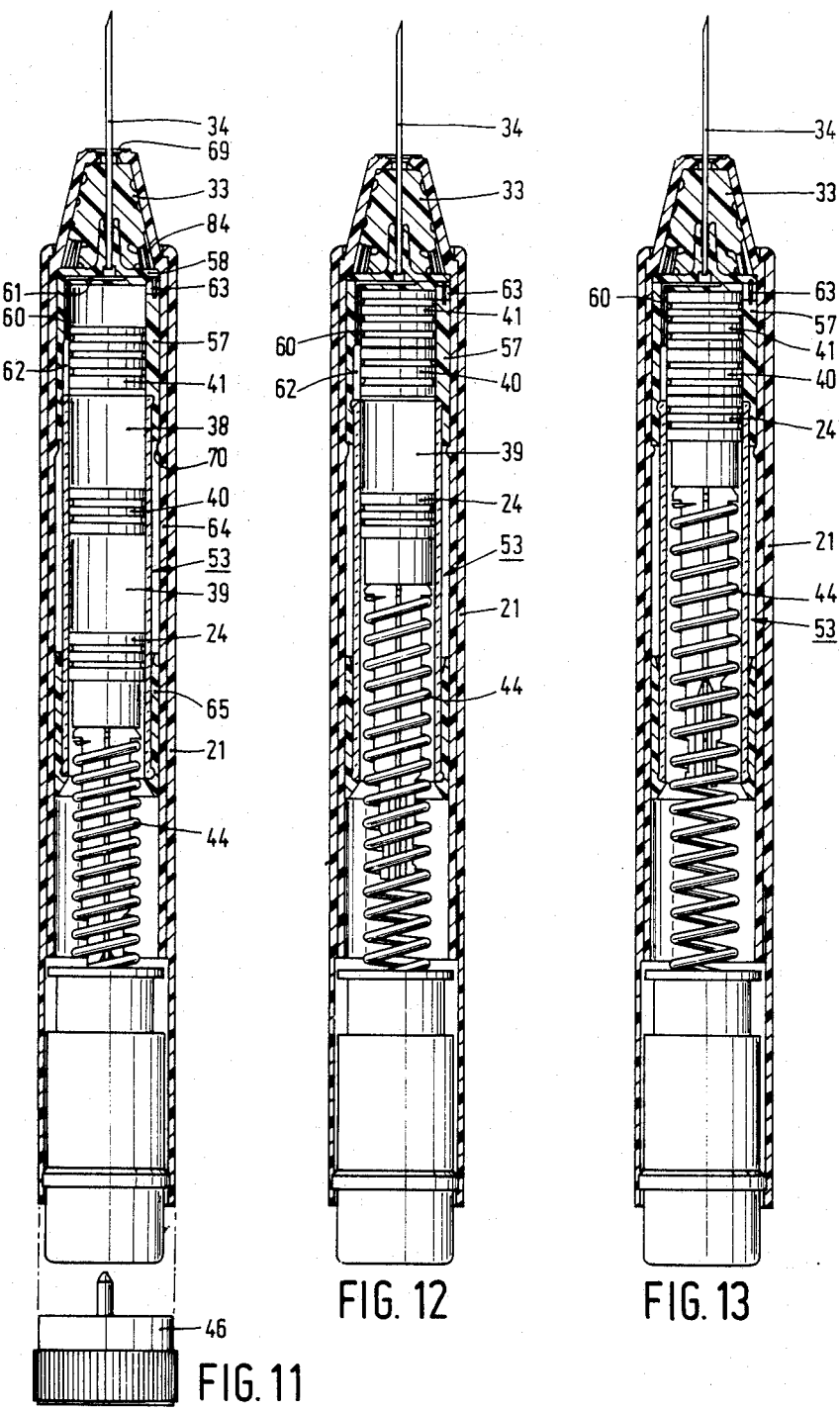
FIGS. 11, 12, and 13 illustrate the operation of the injector shown in FIG. 8, in which the injector is again shown partly in a side elevation and partly in a longitudinal sectional view.

When the injector shown in FIGS. 8–10 is actuated, as shown in FIGS. 11, 12, and 13, of course after removing the safety member 46 and unlocking the discharge mechanism, the cartridge assembly 53, i.e. cartridge holder, barrel with contents, and needle holder, moves forward under the influence of the spring, the clamping sleeve 65 moving slidingly forward in the rear end of the cartridge holder 64. When the needle holder passes, the cartridge holder wall and the wall of the outer sleeve bend slightly outwards at the area of the cams 70 on the cartridge holder wall so as to allow passage of the needle holder ("overridden"). The needle guard 33 is compressed between the front wall of the flange 58 of the neck portion of the needle holder and the longitudinal ridges 84 upon the inner wall of the front end of the tapering nose portion of the cartridge holder 64, the needle 34 piercing the closed end of the needle guard, emanating through the aperture 69 and entering into the body at that place where the injection will be administered. When the injection needle is in its foremost position, in which the needle holder is stopped by a narrowing in the cartridge holder 64, at the area where the nose portions begins, or by the force stored in the compressed needle guard, the forward movement of the piston begins under the influence of the same spring. The air present in the shaft of the needle holder in front of the sealing stopper can escape through the aperture 63 in the shaft. At the instant the sealing stopper 41 has been moved forward over the distance shown in FIG. 11, the entrance 62 to the duct 60 recessed in the wall of the shaft 57 is uncovered for the injection liquid in compartment 38 so that the injection liquid can reach the injection needle 34 via aperture 62, duct 60, and slot 61, and can be injected. At the same time, as is also shown in FIG. 11, the sealing stopper has been moved forward into the shaft of the cartridge holder over such a distance that the front end of the stopper adjoins the inner wall of the shaft in a circumferentially sealing manner and so prevents the injection liquid from reaching the space in front of the sealing stopper.

When all the liquid from compartment 38 has been injected, the front face of the separating stopper 40 engages the rear face of the sealing stopper 41. Under the influence of the spring 44, these stoppers are collectively pushed further forward into the shaft of the needle holder, in which the air present in front of the stoppers can again escape via the aperture 63 in the shaft. When the stoppers have occupied the position shown in FIG. 12, the entrance 62 to duct 60 is uncovered for the injection liquid in compartment 39, which can then leave the injector in the same manner as the first injection liquid.

When all of the injection liquid has been injected, the piston and stoppers engage each other as is shown in FIG. 13. The stoppers then are in the ultimate forward position, in which the front face of the sealing stopper engages the rear face of the front end wall of the needle holder shaft.

The injectors shown in FIGS. 14 and 16 in outline are similar to those shown in FIGS. 1 and 8, respectively, except that the injectors of FIGS. 14 and 16 can accommodate a solid in addition to liquids. Like components are again referred to by the same reference numerals as used in FIGS. 1 and 8. In the injectors shown in FIGS. 14 and 16, the solid is accommodated in compartment 71 between the separating stopper and a passable stopper 72 included in the barrel between the separating stopper and the piston; the passable stopper is, like the piston and other stoppers, manufactured from a resilient material, for example, a rubber of a pharmaceutical quality. In the injector shown in FIG. 16, a rubber molded member 85 having a reduced diameter is accommodated in compartment 71 to reduce the contents of compartment 71 and hence of the air present therein. The solvent for the solid is provided in the compartment 74 between the piston and the passable stopper. The barrel 75 comprises a by-pass in the form of a longitudinal bulge 76, shown more clearly in the cross-sectional view of FIG. 18. Essential are the empty, i.e. not filled with liquid, spaces 77 and 78, respectively, in the barrel in front of the needle holder stopper and sealing stopper in the injectors shown in FIGS. 14 and 16, respectively. When the injector shown in FIG. 14 is made ready for use, the needle holder with injection needle can move forward in this space through which the needle extends before the injector is made ready for use. The air present in this space can escape freely via the aperture in the nose portion of the cartridge holder, which aperture comprises a bacterial filter. When the injector shown in FIG. 16 is made ready for use, the sealing stopper can move forward in the space, and the air in the space can freely escape via the aperture in the shaft of the needle holder, which aperture comprises a bacteria filter.

The injector shown in FIG. 14 is made ready for use by moving the cartridge holder 25 in the outer sleeve backwards. The barrel 75 and the clamping sleeve 42 connected to the rear end of the barrel and slidably accommodated in the outer sleeve are also moved backwards. The discharge mechanism 43 is firmly connected to the outer sleeve 21 by a snap connection 51 so that as a result of this inward movement the barrel contents including the needle holder 30 with needle 34 are moved forwards via a plunger 79 connected to the piston 24 via an elongated sleeve 87. When the passable stopper 72 has been moved forward in the barrel over such a distance that the rear end of the by-pass 76 in the barrel wall has become accessible for the solvent in compartment 74, the solvent flows to the solid in compartment 71, the passable stopper remaining in its place, but the stoppers 40 and 41, as well as the needle holder, moving forward in the barrel. When all the solvent for the solid has been added to the solid, in which solvent the solid can dissolve, the front face of the piston engages the rear face of the passable stopper; this position is shown in FIG. 15. The needle holder stopper 31 now is in the front end of the barrel and the closed front end of the needle guard 33 engages the longitudinal ridges 86 on the inner wall of the front end of the nose portion 28 of the cartridge holder 25. In the position shown in FIG. 15 the cartridge holder 25 is locked in the outer sleeve 21 by means of a plurality of outwardly projecting resilient lug-shaped elements or catches 52 which engage behind the inwardly bent edge at the front end of the outer sleeve and thus prevent a forward movement of the cartridge holder in the outer sleeve. These catches are connected at one end to the outer wall of the cartridge holder and otherwise stand free from the cartridge holder directed forward at an acute angle with the cartridge holder. With the above-described telescoping movement of the cartridge holder with respect to the outer sleeve, the catches are pushed inwards against their spring action during passage through the aperture at the front end of the outer sleeve.

The injector of FIG. 15 made ready for use may be used in the same manner for the administration of an injection as described hereinabove and shown in FIGS. 4, 5, and 6, in which the dissolved solid in compartment 39 is moved forward by the piston 24 together with the passable stopper 72.

The injector shown in FIG. 16 is made ready for use by an inwardly directed movement of the outer sleeve 21 with respect to the outer pistol sleeve 67 movable telescopically in the outer sleeve, in which the radially outwardly projecting cams 81 positioned radially on the outer wall of the pistol sleeve detach from the engagement of the circumferential groove 82 recessed in the inner wall of the outer sleeve. The discharge mechanism 43 is connected to the piston 24 via a plunger 79 with elongated sleeve 87, so that as a result of this inwardly directed movement, the barrel contents are moved forward. When the passable stopper has been moved forward in the barrel over such a distance that the solvent in compartment 74 can reach the solid in compartment 71 via the by-pass 76, all the solvent flows through the by-pass to the solid until the front face of the piston 24 engages the rear face of the passable stopper. In order to prevent the cartridge from moving forward in the cartridge holder while the injector is made ready for use, the sleeve 65 clamped on the rear end of the barrel 75 is provided with a number of resilient abutting cams 83 that engage the rear edge of the cartridge holder 64. In order to lock the cartridge in the cartridge holder, the telescoping movement continues over a small distance until the radially outwardly projecting circumferential ridge 80 on the outer pistol sleeve engages in the groove 82 in the outer sleeve, and the front face of the flange 58 of the neck portion of the needle holder abuts against the cams 70 on the inner wall of the cartridge holder. This is the position shown in FIG. 17, in which the sealing stopper 41 is present in the front end of the barrel and the closed front end of the needle guard 33 engages the longitudinal ridges 84 in the front end of the tapering end portion of the cartridge holder 64. During this last phase of the telescoping movement, the resilient abutting cams 83, which at one end are connected to the wall of the clamping sleeve 65 and for the remaining part are directed forward at an acute angle with the clamping sleeve, are pushed inwards against their spring force by a sleeve-like extension 66 of the inner pistol sleeve 68, where they are taken up in recesses in the clamping sleeve corresponding to the abutting cams. Finally, the front ends of the abutting cams move within the rear end of the cartridge holder, as a result of which a clamping connection of the barrel in the cartridge holder is obtained, so that the cartridge cannot unintendedly move forward in the cartridge holder as a result of a shock.

The injector of FIG. 17 made ready for use may be used in the same manner for the administration of an injection as described above and shown in FIGS. 11, 12, and 13, in which the dissolved solid in compartment 39 is moved forward by the piston 24 together with the passable stopper 72.

It will be apparent to those skilled in the art that various modifications and variations could be made in the automatic injector of the invention without departing from the scope or spirit of the invention.

What is claimed is:

1. An automatic injector for injecting one or more injection liquids, comprising:
   a combination of a substantially cylindrical means containing a discharge mechanism and a plurality of cartridge elements, said cartridge elements comprising:
   a piston that is movable in said substantially cylindrical means and seals same;
   a sealing stopper that is movable in said substantially cylindrical means, whose circumference adjoins the inner wall of said cylindrical means in a sealing manner, and that, prior to use of the injector, seals the foremost injection liquid from the front end of said substantially cylindrical means;
   a number of separating stoppers equal to one less than the number of said liquids, said separating stoppers being movable in said substantially cylindrical means and having circumferences that adjoin the inner wall of said cylindrical means in a sealing manner, thereby keeping said liquids separated from each other prior to use of said injector;

a needle holder comprising a neck for sealingly gripping a needle, and a needle holder stopper that is movable in the substantially cylindrical means, that at its rear end adjoins the front face of said sealing stopper, that at its front end adjoins said neck, that comprises a longitudinal bore that at the front end of said needle holder stopper communicates with the duct of said neck, and that comprises a by-pass means through which said one or more liquids behind said sealing stopper can reach said bore; and a needle sealingly gripped by said neck;

said substantially cylindrical means comprising:

a nose portion that tapers inwardly in the forward direction and terminates at its front end with an aperture to allow passage of said needle during operation of the injector and at its rear end comprises an abutment for said needle holder stopper in its ultimate forward position; and by-pass means in front of said sealing stopper for permitting said one or more liquids behind said sealing stopper to reach said needle holder by-pass means when during operation of the injector the sealing stopper and said number of separating stoppers are moved forward, said cylindrical means by-pass means extending in the longitudinal direction over a length that is substantially shorter than the combined lengths of said sealing stopper and said needle holder stopper;

wherein said substantially cylindrical means and said cartridge elements are so proportioned that when, during operation of said injector, said needle holder stopper has been moved forward, said needle holder stopper circumferentially adjoins in a sealing manner the inner wall of said substantially cylindrical means in front of said cylindrical means by-pass means, and that the distance between the rear end of said cylindrical means by-pass means and said abutment for said needle holder stopper is slightly greater than the combined lengths of said needle holder stopper, said sealing stopper, and said number of separating stoppers, so that when all of said stoppers are in their ultimate forward positions, they do not cover the rear end of said cylindrical means by-pass means.

2. An injector according to claim 1, wherein said substantially cylindrical means comprises a cartridge, a cartridge holder holding said cartridge, and an outer sleeve that can be moved telescopically around said cartridge holder, said cartridge comprising a hollow, substantially cylindrical barrel that is open at each end;

wherein said piston is movable in said barrel and seals said barrel; and said sealing stopper and number of separating stoppers are movable in said barrel and have circumferences that adjoin the inner wall of said barrel in a sealing manner, said sealing stopper sealing the foremost injection liquid from the front end of said barrel;

said cartridge holder comprising:

a collar connected to the front end of said barrel in a sealing manner;

said nose portion; and a hollow shaft between said collar and said nose portion having substantially the same inner diameter as the inner wall of said barrel;

wherein said cylindrical means by-pass means is in the wall of said shaft or in the wall of said barrel in front of said sealing stopper.

3. An injector according to claim 2, wherein said needle holder by-pass means comprises at least one slot radially recessed in the rear face of the needle holder stopper and an adjoining circumferential slot recessed in the same face at the circumferential edge.

4. An injector according to claim 2, wherein said cylindrical means by-pass means is in the wall of said cartridge holder shaft and comprises at least one slot that is recessed in the inner wall of said shaft and extends in the longitudinal direction of said shaft over a length that is substantially shorter than the combined lengths of said sealing stopper and said needle holder stopper.

5. An injector according to claim 2, wherein said cylindrical means by-pass means is in the wall of said barrel and comprises at least one outwardly projecting bulge of said barrel wall extending in the longitudinal direction of said barrel over a length that is substantially shorter than the combined lengths of said sealing stopper and said needle holder stopper.

6. An injector according to claim 1, wherein said sealing stopper and said needle holder comprise a single unitary structure.

7. An injector according to claim 1, further comprising sheath means on said needle to maintain said needle in a sterile condition.

8. An injector according to claim 1, wherein said needle holder comprises a resilient material.

9. An injector according to claim 1, further comprising a bacteria filter in said aperture.

10. An injector according to claim 1, in which prior to use at least two different substances that are not allowed to be in contact with each other for a long period of time can be stored separately, one of said substances being a solid that can be injected as an injection liquid only after dissolution in a solvent, wherein said substantially cylindrical means comprises means containing said cartridge elements and an outer sleeve, said discharge mechanism being in operative relationship to said piston via a plunger and capable of telescoping movement relative to said means containing said cartridge elements, whereby the contents of said means containing said cartridge elements, including said needle holder with said needle, can be moved forward in said means containing said cartridge elements, as a result of which said injector is made ready for use;

said injector further comprising:

between said piston and said sealing stopper a passable stopper that is movable in said means containing said cartridge elements and that prior to making said injector ready for use adjoins the inner wall of said means containing said cartridge elements in a circumferentially sealing manner and keeps said solid separated from said solvent;

a solvent by-pass means for liquid in the wall of said means containing said cartridge elements, said solvent by-pass means being slightly longer than said passable stopper and, when said injector is made ready for use, permitting said solvent to pass the passable stopper and reach said solid in front of said passable stopper and dissolve same, but said solvent by-pass means, prior to making said injector ready for use, being sealed from said solvent present behind said passable stopper by means of said passable stopper; and prior to making said injector ready for use, a space that is not filled with substance and that on its rear and lateral sides is bounded by the front of said needle holder stopper and the inner wall of said means containing said cartridge elements, said empty space being so proportioned that the distance between the front end of said injection needle and said aperture in said nose portion is at least as long as the distance from the front face of said piston or, in the presence of a separating stopper behind the passable stopper, of said separating stopper to the rear end of said solvent by-pass means.

11. An injector according to claim 10, wherein said means containing said cartridge elements comprises a cartridge and a cartridge holder holding said cartridge, said cartridge comprising:
a hollow, substantially cylindrical barrel that is open at each end; wherein said piston is movable in said barrel and seals said barrel; and said sealing, number of separating, and passable stoppers are movable in said barrel and have circumferences that adjoin the inner wall of said barrel in a sealing manner, said sealing stopper sealing the foremost injection liquid from the front end of said barrel;
said cartridge holder comprising:
a collar connected to the front end of said barrel in a sealing manner;
said nose portion; and
a hollow shaft between said collar and said nose portion having substantially the same inner diameter as the inner wall of said barrel;
wherein said cylindrical means by-pass means is in the wall of said shaft or in the wall of said barrel in front of said sealing stopper, and wherein said empty space is bounded on its lateral sides by the inner wall of said barrel, said empty space in the barrel through which said injection needle extends being at least as long as the distance from the front face of said piston or, in the presence of a separating stopper behind the passable stopper, of said separating stopper to the rear end of said solvent by-pass means.

12. An automatic injector for injecting one or more injection liquids, comprising:
a combination of a discharge mechanism, a cartridge holder, and a cartridge that is slidably positioned in said cartridge holder, said cartridge comprising:
a hollow, substantially cylindrical barrel that is open at each end;
a piston that is movable in said barrel and seals same;
a sealing stopper that is movable in said barrel, whose circumference sealingly adjoins the inner wall of said barrel, and that, prior to use of the injector, seals the foremost injection liquid from the front end of said barrel,
a number of separating stoppers equal to one less than the number of said liquids, said separating stoppers being movable in said barrel and having circumferences that adjoin the inner wall of said barrel in a sealing manner, thereby keeping said liquids separated from each other in said barrel prior to use of said injector;
a needle holder comprising:
(i) a collar connected to the front end of said barrel in a sealing manner;
(ii) a neck for sealingly gripping a needle;
(iii) a hollow, substantially cylindrical shaft between said collar and said neck;
(iv) a by-pass in the wall of said shaft, through which said one or more liquids behind said sealing stopper can reach the injection needle when during operation of the injector the stopper or stoppers is or are moved forward into said shaft of said needle holder, said bypass comprising at least one duct recessed in the wall of said shaft and communicating the space in the shaft bounded by the inner wall of the shaft and the rear face of the neck with the neck aperture of said needle holder, said duct, from approximately the rear edge of said shaft over a part of the length of said shaft substantially shorter than the length of said sealing stopper, being in open communication with said space in said shaft, but for the remaining part being separated from said space; and
(v) at the front end of said shaft, at least one aperture recessed in the wall of said shaft, said aperture communicating said space in said shaft with the interior of said cartridge holder; and
a needle sealingly gripped by said neck;
wherein said shaft is so proportioned that said space bounded by the inner wall of the shaft and the rear face of the neck, apart from said by-pass, has approximately the same diameter as the inner wall of said barrel and is slightly longer than the combined lengths of said sealing stopper and said number of separating stoppers, so that said sealing and separating stoppers in the ultimate forward position can fill said space substantially entirely but do not cover the end of said by-pass adjoining said barrel.

13. An injector according to claim 12, further comprising an outer sleeve that can be moved telescopically around the cartridge holder.

14. An injector according to claim 13, in which prior to use at least two different substances that are not allowed to be in contact with each other for a long period of time can be stored separately, one of said substances being a solid that can be injected as an injection liquid only after dissolution in a solvent, wherein said discharge mechanism is in operative relationship to said piston via a plunger and is capable of telescoping movement relative to said cartridge holder, whereby the contents of said barrel can be moved forward in said barrel so that said injector is made ready for use;
said injector further comprising:
between said piston and said sealing stopper a passable stopper that is movable in said barrel and that prior to making the injector ready for use adjoins the inner wall of said barrel in a circumferentially sealing manner and keeps said solid separated from said solvent;
solvent by-pass means for liquid in the wall of said barrel, said solvent by-pass means being slightly longer than said passable stopper and, when said injector is made ready for use, permitting said solvent to pass the passable stopper and reach said solid in front of said passable stopper and dissolve same, but said solvent by-pass means, prior to making said injector ready for use, being sealed from said solvent present behind said passable stopper by means of said passable stopper;
prior to making said injector ready for use, a space that is not filled with substance and that is bounded on its rear and lateral sides by the front face of said sealing stopper and the inner wall of said barrel, and that on its front side is in open communication with the space in the shaft of said needle holder, said empty space in said barrel being at least as long as the distance from the front face of said piston or, in the presence of a separating stopper behind said passable stopper, of said separating stopper to the rear end of said solvent by-pass means; and means for preventing said cartridge in said cartridge holder from moving forward when said injector is made ready for use.

15. An injector according to claim 12, wherein said needle is covered by a sheath to maintain said needle in a sterile condition.

16. An injector according to claim 12, wherein said at least one aperture recessed in the wall of said shaft comprises a bacteria filter.

17. An injector according to claim 12, wherein:

said needle holder comprises two portions, the first portion comprising said collar and said shaft, the other portion comprising said neck, said shaft being closed at its front end by means of an end wall and said by-pass in the wall of said shaft being formed by at least one duct recessed in the side wall of said shaft and extending in the longitudinal direction thereof, said duct communicating with at least one slot radially recessed in the front face of said end wall, and said neck portion of said needle holder comprising a flange having an approximately equally large diameter as the end wall of said shaft, by means of which flange said neck portion at its circumferential edge is sealingly connected to the front face of the end wall of said shaft in such a way that said neck aperture communicates with said at least one slot recessed in the front face of said end wall; and said at least one aperture in the wall of said shaft is recessed in the front end of said side wall or where the side wall and said end wall adjoin each other.

18. An injector according to claim 11 or claim 14, wherein a molded member of an inert material is provided in the space in said barrel provided for said solid, or the front of the passable stopper and/or the rear of the sealing stopper or separating stopper is/are elongated by a cylindrical part having a reduced diameter, to reduce the volume of said space.

19. An injector according to claim 11 or claim 14, wherein said solvent by-pass means in said barrel wall comprises at least one slot recessed in the inner wall of said barrel and extending in the longitudinal direction of said barrel over a length that slightly exceeds the length of said passable stopper.

20. An injector according to claim 11 or claim 14, wherein the inner wall of said barrel at the area of said solvent by-pass means comprises at least one ridge that extends in the longitudinal direction of said barrel over a length that slightly exceeds the length of said passable stopper, so that, when said injector is made ready for use, said stopper is deformed by contact with said ridge, a by-pass for the solvent behind the said passable stopper being formed, through which said liquid can pass the stopper.

21. An injector according to claim 11 or claim 14, wherein the wall of said barrel at the area of said solvent by-pass means is deformed over a length that slightly exceeds the length of said passable stopper, so that, when said injector is made ready for use, the solvent behind said stopper can pass the stopper at the area of the deformation.

22. An injector according to claim 21, wherein said deformation of the wall of said barrel comprises at least one outwardly projecting longitudinal bulge of the barrel wall through which, when the injector is made ready for use, the solvent behind the passable stopper can reach the solid in front of said stopper.

23. An injector according to claim 21, wherein said deformation of the wall of said barrel consists of at least one inwardly projecting longitudinal ridge of the barrel wall by which, when the injector is made ready for use, the passable stopper is deformed by contact with said ridge, a by-pass for the solvent behind the passable stopper being formed through which said liquid can reach along said stopper the solid in front of the stopper.

24. An injector according to claim 21, wherein at the area of said deformation the barrel wall has an oval cross-section, through which, when the injector is made ready for use, the solvent behind the passable stopper can reach the solid in front of said stopper.

25. An injector according to claim 11 or claim 14, wherein said outer sleeve is capable of telescoping movement around said cartridge holder, and wherein said discharge mechanism is connected to said outer sleeve.

26. An injector according to claim 11 or claim 14, wherein said outer sleeve is telescopically connected to said discharge mechanism.

27. An injector according to claim 26, wherein said discharge mechanism comprises a coil spring as a power source, the rear end of which is accommodated in an inner pistol sleeve that is slidably provided in an outer pistol sleeve; the rear end of said outer sleeve is provided around said outer pistol sleeve so as to be telescopically slidable; and means are provided to lock said outer pistol sleeve in said outer sleeve after having made said injector ready for use.

28. An injector according to claim 27, wherein said locking means comprises a radially outwardly projecting circumferential ridge or a plurality of radially located cams on the outer wall of said outer pistol sleeve, which ridge or which number of cams engages in a circumferential groove in the inner wall of the rear end of said outer sleeve.

29. An injector according to claim 26, wherein said means for preventing said cartridge in said cartridge holder from moving forward while making said injector ready for use comprises a plurality of resilient abutting cams that are connected to a sleeve clamped around the rear end of said barrel, that engage the rear edge of said cartridge holder, and that, when said injector has been made ready for use, are unlocked by a force directed oppositely to the resilience of the abutting cams.

30. An injector according to claim 25, further comprising means to lock said cartridge holder in said outer sleeve after having made the injector ready for use.

31. An injector according to claim 30, wherein said locking means comprise a plurality of outwardly projecting resilient lug-shaped elements or catches engaging behind an inwardly bent edge at the front end of said outer sleeve and thus preventing a forward movement of said cartridge holder in said outer sleeve, the elements or catches being connected at one end to the outer wall of the cartridge holder and otherwise being directed forward and standing free from said cartridge holder at an acute angle with the cartridge holder wall.

* * * * *